US010124049B2

(12) United States Patent
Yang

(10) Patent No.: US 10,124,049 B2
(45) Date of Patent: Nov. 13, 2018

(54) ACINETOBACTER BAUMANNII ANTIGENS AND THE USES THEREOF

(71) Applicant: National Chung Hsing University, Taichung (TW)

(72) Inventor: Chiou-Ying Yang, Taichung (TW)

(73) Assignee: NATIONAL CHUNG HSING UNIVERSITY, Taichung (TW)

( * ) Notice: Subject to any disclaimer, the term of this patent is extended or adjusted under 35 U.S.C. 154(b) by 0 days.

(21) Appl. No.: 15/177,184

(22) Filed: Jun. 8, 2016

(65) Prior Publication Data

US 2016/0361406 A1 Dec. 15, 2016

(30) Foreign Application Priority Data

Jun. 11, 2015 (TW) .............................. 104118940 A

(51) Int. Cl.
| | |
|---|---|
| C07K 16/12 | (2006.01) |
| A61K 39/02 | (2006.01) |
| A61K 39/05 | (2006.01) |
| G01N 33/569 | (2006.01) |
| C07K 14/22 | (2006.01) |

(52) U.S. Cl.
CPC .......... *A61K 39/0208* (2013.01); *A61K 39/05* (2013.01); *C07K 14/22* (2013.01); *C07K 16/1214* (2013.01); *C07K 16/1217* (2013.01); *G01N 33/56911* (2013.01); *C07K 2317/73* (2013.01); *G01N 2333/22* (2013.01); *G01N 2469/10* (2013.01)

(58) Field of Classification Search
None
See application file for complete search history.

(56) References Cited

U.S. PATENT DOCUMENTS 6,562,958 B1 5/2003 Breton et al.

OTHER PUBLICATIONS

Ralph Pantophlet et al., "Identification of Acinetobacter Isolates from Species Belonging to the Acinetobacter calcoaceticus-Acinetobacter baumannii Complex with Monoclonal Antibodies Specific for O Antigens of Their Lipopolysaccharides", Clinical and Diagnostic Laboratory Immunology, Jan. 2002, p. 60-65.

*Primary Examiner* — Brian Gangle
(74) *Attorney, Agent, or Firm* — WPAT, PC

(57) ABSTRACT

The present invention relates to an isolated polypeptide antigen of *Acinetobacter baumannii*, comprising at least an amino acid sequence selected from the group consisting of: (a) SEQ ID NOs: 1-5; (b) an amino acid sequence having at least 80% sequence identity to SEQ ID NOs: 1, 3, 4 or 5; (c) an amino acid sequence having at least 60% sequence identity to SEQ ID NO: 2; and (d) a fragment of the amino acid sequence according to (a) to (c); wherein the polypeptide having the amino acid sequence according to (b) to (d) has immunostimulatory activity. The universal polypeptide antigens of *Acinetobacter baumannii* can be used in the universal vaccine preparation. The corresponding antibodies can be used in the diagnostic and treatment of *Acinetobacter baumannii*.

3 Claims, 6 Drawing Sheets

Specification includes a Sequence Listing.

ACINETOBACTER BAUMANNII ANTIGENS AND THE USES THEREOF

CROSS-REFERENCE TO RELATED APPLICATION

This application claims the priority of Taiwanese patent application No. 104118940, filed on Jun. 11, 2015, which is incorporated herewith by reference.

BACKGROUND OF THE INVENTION

1. Field of the Invention

The present invention relates to the antigen used to elicit immune response, more particularly, relates to the polypeptide antigen against *Acinetobacter baumannii*. The present invention further relates to the vaccine composition comprising the polypeptide antigen against *Acinetobacter baumannii* and the antibody specifically bound to the polypeptide antigen of *Acinetobacter baumannii*. Moreover, the present invention relates to the isolated nucleic acid encoding the polypeptide antigen of *Acinetobacter baumannii*, the expression vector containing the isolated nucleic acid, and the host cell containing the expression vector.

2. The Prior Arts

*Acinetobacter* spp. are widely distributed in nature. They are gram-negative bacteria and are approximately divided into 20 species. Among them, *Acinetobacter baumannii* is the most general and well-studied. They can survive on a variety of surfaces, whether wet or dry, and have become one of the most common nosocomial pathogens in the hospital. *Acinetobacter baumannii* is an opportunistic human pathogen. Normally, it is nonpathogenic to a healthy individual, while it would cause severe clinical disease when the individual is with compromised immune systems.

In general, *Acinetobacter baumannii* is found on various objects or devices in a hospital, such as gloves, syringes, needles, carts, respirators, beds, cabinets, sinks, floor, and outlets of air conditioner, even in a stethoscope or medical records. Particularly, *Acinetobacter baumannii* often appears in the warm and humid environments such as drinking water, food, and drainage channels as well as in/on the human body, such as skin, armpits, conjunctiva, oral cavity, upper respiratory tract, nasopharynx, gastrointestinal tract, urethra, etc. The patients or their families contacted with these bacteria are generally got sick when their immune system becomes weak. In particular, during invasive treatments such as intubation or surgery, the patients would have higher risk been infected by these opportunistic pathogens. Thus, the probability of nosocomial infection has increased and thus become a serious health problem concerning the patients and the health care.

Generally, antibiotics are usually used for the treatment of bacterial infection. However, due to the overuse of antibiotics, some bacteria gradually become resistant to which and are difficult to eliminate. The way to overcome this problem is to treat with different antibiotics or apply new but expensive antibiotics. If there is no effective way to inhibit the evolution of resistance of bacteria to drugs, no available antibiotics for curing the bacterial infection will arrive in the near feature. Regarding *Acinetobacter baumannii* which causes nosocomial infections, many multi-drug resistant strains thereof have been isolated. Since they can survive for some time on the surface of an object, there is a need to provide a proper treatment or prevention method so that the problem of nosocomial infection can be reduced.

To vaccinate subjects to generate the protection against bacterial infection may be an effective way to solve the problem described above. Most vaccines are produced by inactivated or attenuated pathogens and then the whole treated pathogens are injected into an individual. The immunized individual responds by producing both a humoral (i.e., antibody) and cellular (i.e., cytotoxic, helper or regulatory T cell) response, thereby the pathogen invading a host later can be neutralized and cleared. However, the use of attenuated or inactivated pathogen vaccines for the prevention of diseases may be dangerous, especially when the pathology and attenuation nature thereof are not clear. Thus, a vaccine composition comprising the antigens of pathogen epitopes which can stimulate an immune response, rather than introducing the whole pathogen, is currently one of the main methods for preparation of safer vaccines.

However, identification of specific antigens to prepare the vaccine is difficult. In previous studies, Pantophlet et al. has identified *Acinetobacter* strains by lipopolysaccharide O antigen and corresponding antibodies (Pantophlet R. et al., Clinical and Diagnostic Laboratory Immunology, 9, 60-65, 2002), but which have not disclosed other antigens and any vaccine applications thereof. Although U.S. Pat. No. 6,562, 958 has disclosed about 4000 nucleotide and amino acid sequences relating to *Acinetobacter baumannii*, however, they are mostly with unidentified function and whether the gene can be expressed or not is unknown. Therefore, to prevent and diagnose *Acinetobacter baumannii* infection, there is an urgent need to find the target antigens to elicit immune response efficiently and specific antibodies used in diagnostic and treatment of *Acinetobacter baumannii* infection.

SUMMARY OF THE INVENTION

In view of the above reasons, an objective of the present invention is to provide an universal polypeptide antigen of *Acinetobacter* strains for preparing vaccine composition to elicit protective immunity against *Acinetobacter baumannii* infection or infection by other pathogens having similar antigens. Another objective of the present invention is to provide an antibody specifically directed against the previous described polypeptide antigens for diagnostic or treatment of a subject infected with *Acinetobacter baumannii*.

In order to fulfill above objectives, an isolated polypeptide antigen of *Acinetobacter baumannii* is provided. The isolated polypeptide antigen comprising at least an amino acid sequence selected from the group consisting of: (a) SEQ ID NOs: 1-5; (b) an amino acid sequence having at least 80% sequence identity to SEQ ID NOs: 1, 3, 4 or 5; (c) an amino acid sequence having at least 60% sequence identity to SEQ ID NO: 2; and (d) a fragment of the amino acid sequence according to (a) to (c); wherein the polypeptide having the amino acid sequence according to (b) to (d) has immunostimulatory activity. The amino acid sequences of SEQ ID NOs: 1-5 are referred to sequence listing.

In an embodiment of the present invention, an antibody directed against *Acinetobacter baumannii* is provided. The antibody specifically binds to the above-mentioned polypeptide antigen, wherein the antibody may be a polyclonal antibody or monoclonal antibody. Besides normally intact antibody structure having two light chains and two heavy chains, the antibody can also be the antibody fragment thereof but recognizing the same antigen. Example of the antibody fragment includes, but not limited to, Fab, F(ab')$_2$, Fv or ScFv antibody.

In an embodiment of the present invention, a pharmaceutical composition comprising the above-mentioned antibody and a pharmaceutically acceptable carrier is provided.

In another embodiment of the present invention, a method for detecting an *Acinetobacter baumannii* is provided. The method comprising the steps of providing the antibody, wherein the antibody can specifically bind to the polypeptide antigen; contacting the antibody with a specimen; detecting and analyzing a immune complex formed by the antibody and the polypeptide antigen on *Acinetobacter baumannii* with regents or instruments to determine the presence of *Acinetobacter baumannii* in the specimen. The determined method can be Western blot, ELISA or common skills based on immune reaction in the art.

In further embodiment of the present invention, a diagnostic kit for detection of *Acinetobacter baumannii* comprising the above-mentioned antibody is also provided.

In yet another embodiment, the preset invention provides a method for preventing bacterial infections by vaccinating a subject a polypeptide antigen described above. In further embodiment, the preset invention also provides a vaccine composition comprising at least one polypeptide antigen of *Acinetobacter baumannii*. The vaccine composition can further comprise a pharmaceutically acceptable carrier or an adjuvant. The definition of "pharmaceutically acceptable carrier" is meant to encompass any carrier, which does not interfere with effectiveness of the biological activity of the active ingredient and is not toxic to the host been administered. The pharmaceutically acceptable carrier may include, but are not limited to: diluents, stabilizers, preservatives, antioxidants, dispersing agents, solubilizing agents, antibacterial agents, antifungal agents, adjuvant and immunostimulatory agents, and any combinations thereof. The term "adjuvant" as used herein refers to a substance distinct from target antigen that is capable of increasing the antigenic response. The adjuvant may be, but are not limited to Gerbu adjuvant, *Corynebacterium* or mycobacteria, cholera toxin, tetanus toxoid, or a variety of oil-water emulsions (e.g., IDEC-AF). In addition, the adjuvant may also include mineral salts or mineral gels (e.g., aluminum hydroxide, aluminum phosphate and calcium phosphate), surface active substances (e.g., lysolecithin) and immunostimulatory molecules (e.g., saponin), oligonucleotides, interleukin-2 and so on.

To obtain the polypeptide antigen described above, in an embodiment of the present invention, an isolated nucleic acid for encoding a polypeptide antigen of *Acinetobacter baumannii* is provided. The isolated nucleic acid encoding a polypeptide antigen of *Acinetobacter baumannii* comprising an amino acid sequence selected from the group consisting of: (a) SEQ ID NOs: 1-5; (b) an amino acid sequence having at least 80% sequence identity to SEQ ID NOs: 1, 3, 4 or 5; (c) an amino acid sequence having at least 60% sequence identity to SEQ ID NO: 2; and (d) a fragment of the amino acid sequence according to (a) to (c); wherein the polypeptide having the amino acid sequence according to (b) to (d) has immunostimulatory activity.

In one aspect, the isolated nucleic acid can has a nucleotide sequence selected from the group consisting of SEQ ID NOs: 6-10.

In further embodiment of the present invention, an expression vector is provided. The nucleic acid encoding the polypeptide antigen can be cloned into the expression vector, linked with a transcription regulating factor, for expression the needed polypeptide antigen. The transcription regulating factor can regulate directly, for example acts on operon (e.g., lac operon) to initiate transcription, or regulate indirectly on enzymes (e.g., polymerases) needed for transcription or translation. Finally the above-mentioned polypeptide antigen was expressed.

In further embodiment of the present invention, a host cell transformed with the expression vector or a nucleic acid so as to express the polypeptide antigen is provided.

In further embodiment, the present invention provides a diagnostic kit for detecting *Acinetobacter baumannii*. A diagnostic kit comprises a primer pair, wherein the primer pair amplifies a template nucleic acid in a specimen containing *Acinetobacter baumannii* to produce a nucleic acid or a fragment thereof with a PCR method. The primers may amplify the full length of the nucleic acid of *Acinetobacter baumannii* or part of that. Accordingly, *Acinetobacter baumannii* can not only be detected by antibodies directed against but also DNA thereof so that the objective to monitor *Acinetobacter baumannii* is achieved.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENTS

Figure 1:
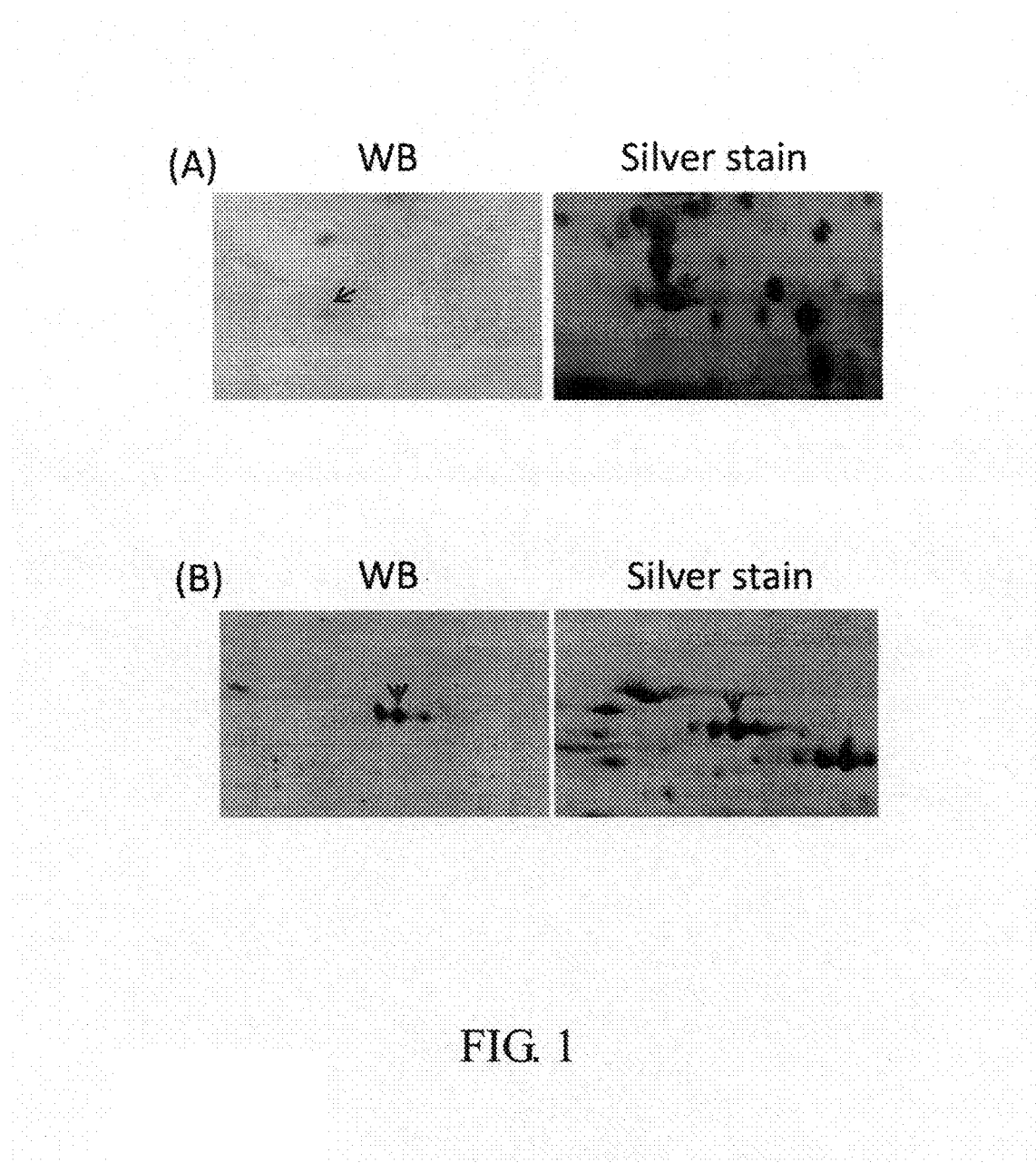
FIG. 1 shows the results of 2D electrophoresis analyzed with Western blot and silver stain for detection of the antigens with immunity-inducing activity in *Acinetobacter baumannii* outer membrane according to Example 1 of the present invention. (A) and (B) shows the results reacted by different human sera. In each figure, the left and right panels are the results of Western blot analysis and silver stain, respectively. Arrows represent the immunoactive spots.

The present invention provides an isolated polypeptide antigen of *Acinetobacter baumannii*. The isolated polypeptide antigen comprising at least a amino acid sequence selected from the group consisting of: (a) SEQ ID NOs: 1-5; (b) an amino acid sequence having at least 80% sequence identity to SEQ ID NOs: 1, 3, 4 or 5; (c) an amino acid sequence having at least 60% sequence identity to SEQ ID NO: 2; and (d) a fragment of the amino acid sequence according to (a) to (c); wherein the polypeptide having the amino acid sequence according to (b) to (d) has immunostimulatory activity.

Sequence identity numbers (SEQ ID NOs) for the amino acid and corresponding nucleotide sequences of the polypeptide antigens are listed in Table 1. The detail nucleotide or amino acid sequence information of each sequence identity number is listed in the Sequence Listing.

TABLE 1

| Polypeptides | Amino acid sequences | nucleotide sequences |
|---|---|---|
| NcsP | SEQ ID NO: 1 | SEQ ID NO: 6 |
| TonB-R | SEQ ID NO: 2 | SEQ ID NO: 7 |
| Pase1 | SEQ ID NO: 3 | SEQ ID NO: 8 |
| Pase2 | SEQ ID NO: 4 | SEQ ID NO: 9 |
| GP1 | SEQ ID NO: 5 | SEQ ID NO: 10 |

SEQ ID NOs: 1-5 are the amino acid sequences of polypeptides which serve as polypeptide antigens according to Examples of the present invention, while SEQ ID NOs: 6-10 are the nucleotide sequences corresponding to SEQ ID NOs: 1-5. In an embodiment, the polypeptide antigen can have an amino acid sequence selected from the group consisting of (a)-(d), or combination thereof and has immunostimulatory activity. In addition to any amino acid sequence set forth in SEQ ID NOs: 1-5, the polypeptide antigen can also have an amino acid sequence which is 20% or less of substitution, deletion or addition based on the full length of an amino acid sequence set forth in any one of SEQ ID NOs: 1, 3, 4 and 5, or an amino acid sequence which is 40% or less of substitution, deletion or addition based on the full length of an amino acid sequence set forth in SEQ ID NO: 2. In addition, the polypeptide antigen can also be a fragment of the full length polypeptide or derivates thereof.

The term "isolated" as used herein refers to a pattern or composition of an object which is different from that in nature environment and is isolated or purified from nature environment or produced by artificial methods.

The term "antigen" as used herein refers to a material being capable of inducing an immune response in a subject, namely a material having immunostimulatory activity. The term "immunostimulatory activity" as used herein refers to inducing an initial immune response such as humoral (i.e., antibody) or/and cellular (i.e., cytotoxic, helper or regulatory T cell) response when administrating an antigen into a subject. As such, the antigen is recognized and bound, and is finally cleared. Generally, the immune response can be elicited by only antigens, or be increased by the assistance of the adjuvant. Therefore, a "polypeptide antigen of *Acinetobacter baumannii*" as used herein refers to an antigen which is a polypeptide or an analog thereof and is capable of inducing above-mentioned immune response.

The term "substitution, deletion or addition of an amino acid sequence" as used herein refers to substituting one or more amino acids of original amino acid sequence, deleting one or more amino acids from original amino acid sequence, adding one or more amino acids into original amino acid sequence or modifying by combination thereof. The modified analogs have predetermined identity with original amino acid sequence. In general, based on the full length of an amino acid sequence set forth in any one of SEQ ID NOs: 1, 3, 4 and 5, 20% or less of substitution, deletion or addition is performed, preferably 10% or less, more preferably 5% or less, and most preferred 1-5 amino acids; namely, the degree of identity of sequence is 80% or more. In addition, based on the full length of an amino acid sequence set forth in any one of SEQ ID NO: 2, 40% or less of substitution, deletion or addition is performed, preferably 20% or less, more preferably 5% or less, and most preferred 1-5 amino acids; namely, the degree of identity of sequence is 60% or more.

The term "fragment of a polypeptide" as used herein refers to a part of original amino acid sequence or combination of parts thereof. It does not comprise the deletion of 20% or 40% or less mentioned above.

The identity of amino sequences can be determined by known software in the art; for example, BLAST method described by Altschul et al. (Nucleic Acids Res. 25:3389-3402, 1997). The BLAST software can be obtained from the National Center for Biotechnology Information (NCBI, http://www.ncbi.nlm.nih.gov).

For the objectives of the present invention, the tBLAST algorithm with the following default settings is used: Expect threshold: 10; word size: 3; Max matches in a query range: 0; Matrix: BLOSUM62; Existence: 11, Extension: 1; Compositional adjustments: conditional compositional score matrix adjustment; Filter: Low complexity regions selected; Mask: not selected.

The term "*Acinetobacter baumannii*" as used herein refers to *Acinetobacter baumannii* species as classified in *Acinetobacter* Molecular Biology (Ed.: Ulrike Gerischer, Caister Academic Press, 2008). *Acinetobacter baumannii* species comprise ATCC 17978, and 6200, SDF . . . etc. recited in Table 2. References and information regarding these strains can be received on the Pubmed homepage (http://www.ncbi.nlm.nih.gov/Taxonomy).

Table 2 below shows the conservation of amino acid sequence identity of proteins encoded by various *Acinetobacter baumannii* strains. The five polypeptides according to the present invention, namely NcsP, TonB-R, Pase1, Pase2 and GP1 are respectively compared to 29 other homologous polypeptides encoded by different *Acinetobacter baumannii* strains. In view of the Table 2, the identities between respective NcsP, TonB-R, Pase1, Pase2 and GP1 and various homologous polypeptides are mostly as high as 98-99%, while only part of TonB-R whose identities between homologous polypeptides are 60% or more. The high degree of amino acid sequence identity of the homologous proteins in various *Acinetobacter baumannii* strains shows that the polypeptides according to the present invention have broad specificity, and thus have high therapeutic values. Keeping with serum bactericidal assay and active protection assay in a mouse, the results thereof indicate that the five polypeptides according to the present invention can be determined as good universal polypeptide antigens for preparing vaccines to prevent *Acinetobacter baumannii* infection.

TABLE 2

| | Polypeptide antigens | | | | |
|---|---|---|---|---|---|
| Strains | NcsP | TonB-R | Pase1 | Pase2 | GP1 |
| 6200 | 99% | 60% | 95% | 99% | 98% |
| SDF | 99% | 60% | 98% | 98% | 97% |
| ZW85-1 | 99% | 61% | 96% | 99% | 99% |
| AB307-0294 | 99% | 99% | 95% | 99% | 99% |
| AB031 | 99% | 61% | 96% | 98% | 99% |
| AC30 | 99% | 99% | 99% | 98% | 99% |
| AC12 | 99% | 99% | 99% | 98% | 99% |
| AbH12O-A2 | 99% | 61% | 98% | 98% | 98% |
| ACICU | 99% | 99% | 99% | 98% | 99% |
| A1 | 99% | 99% | 95% | 99% | 99% |

TABLE 2-continued

| | Polypeptide antigens | | | | |
|---|---|---|---|---|---|
| Strains | NcsP | TonB-R | Pase1 | Pase2 | GP1 |
| BJAB0868 | 99% | 99% | 99% | 98% | 99% |
| AC29 | 99% | 99% | 99% | 98% | 99% |
| 1656-2 | 99% | 99% | 99% | 98% | 99% |
| AYE | 99% | 99% | 95% | 99% | 99% |
| BJAB07104 | 99% | 99% | 99% | 98% | 99% |
| TYTH-1 | 99% | 99% | 99% | 98% | 99% |
| MDR-TJ | 99% | 99% | 99% | 98% | 99% |
| ATCC 17978 | 99% | 61% | 98% | 100% | 100% |
| MDR-ZJ06 | 99% | 99% | 99% | 98% | 99% |
| IOMTU 433 | 99% | 99% | 95% | 99% | 99% |
| BJAB0715 | 99% | 60% | 98% | 96% | 99% |
| NCGM 237 | 99% | 99% | 99% | 98% | 99% |
| TCDC-AB0715 | 99% | 99% | 99% | 98% | 99% |
| PKAB07 | 99% | 99% | 99% | 98% | 99% |
| AB030 | 99% | 61% | 98% | 98% | 98% |
| LAC-4 | 99% | 56% | 98% | 96% | 99% |
| AB0057 | 99% | 99% | 95% | 99% | 99% |
| 6411 | 96% | 97% | 78% | 97% | 92% |
| D1279779 | 99% | 61% | 96% | 94% | 99% |

The polypeptide served as an antigen of *Acinetobacter baumannii* can be prepared by common genetic engineering methods in the art. The DNA encoding the polypeptide is amplified by PCR and then cloned into an expression vector (See Sambrook et al., Molecular Cloning: A-Laboratory Manual, Cold Spring Harbor Press, N.Y., Second (1998) and Third (2000) Edition; Gene Expression Technology, Methods in Enzymology, Genetics and Molecular Biology, Methods in Enzymology, Guthrie & Fink, Academic Press, San Diego, Calif., 1991, and Hitzeman et al., J. Biol. Chem., 255:12073-12080, 1990). Moreover, the polypeptide can also be synthesized with the other known methods in the art.

According to the present invention, the polypeptide antigen is identified by immunoproteomic approach and reverse vaccinology. Following will be the detail description regarding the screening, identification of the polypeptide antigen of *Acinetobacter baumannii*, and the immunity thereof.

Example 1

Screening and Identification of Antigens NcsP and TonB-R

The antigens NcsP and TonB-R were identified by immunoproteomic approach in this example. First, the blood of the patients was collected, and the serum was obtained by centrifuge. Then, the Western blot analysis was performed by using the antiserum to react with total proteins of Taiwan *Acinetobacter baumannii* clinical isolates and the serum with antibodies specifically directed against *Acinetobacter baumannii* was identified (hereinafter referred to as HS-AB). In addition, the *Acinetobacter baumannii* outer membrane protein was extracted and isolated, and 2D electrophoresis thereof was performed. One of two copies of electrophoresis gels obtained was then performed silver staining and the other one was immunodetected by the HS-AB. The results are shown in FIG. 1. By comparing the gels of Western blotting and silver stain, the protein on silver stain corresponding to the immunoactive spot on Western blotting was recovered and subjected to mass spectrometric (MS) analysis. The result of MS shows that the target proteins with highest scores are putative LysM domain superfamily of AB SDF strain (YP_001707847) and outer membrane receptor of AB ACICU strain (YP_001845144), respectively. Based on the characteristic of sequence, YP_001707847 is predicted to be a nonclassical secretory protein, and YP_001845144 is predicted to be a putative ferric siderophore receptor protein.

To confirm that whether these two antigens be recognized by HS-AB, procedures of gene cloning and expression were performed. First, the primers for PCR were designed in accordance with the DNA sequence encoding YP_001707847 and YP_001845144. The above-mentioned Taiwan *Acinetobacter baumannii* clinical isolates were provided as templates and then the colony-PCR was performed by previously described primers. The amplified DNA products encoding these two antigens were respectively cloned into pGEM-T Easy for sequencing. As the sequence listing shows, the identity between the former amplified DNA sequence (SEQ ID NO: 6) and YP_001707847 is 98%, while between the latter amplified DNA sequence (SEQ ID NO: 7) and YP_001845144 is as high as 99%. On the other hand, in comparison with the amino acid sequence encoded by previous DNA sequence, the identity between the former amino acid sequence (SEQ ID NO: 1) and YP_001707847 is 99%, while between the latter amino acid sequence (SEQ ID NO: 2) and YP_001845144 is as high as 99%. The results show that the expressible proteins screened should be YP_001707847 and YP_001845144. Thus, the polypeptides having sequences set forth in SEQ ID NO: 1 and 2 are hereinafter referred to "NcsP" and "TonB-R".

Figure 2:
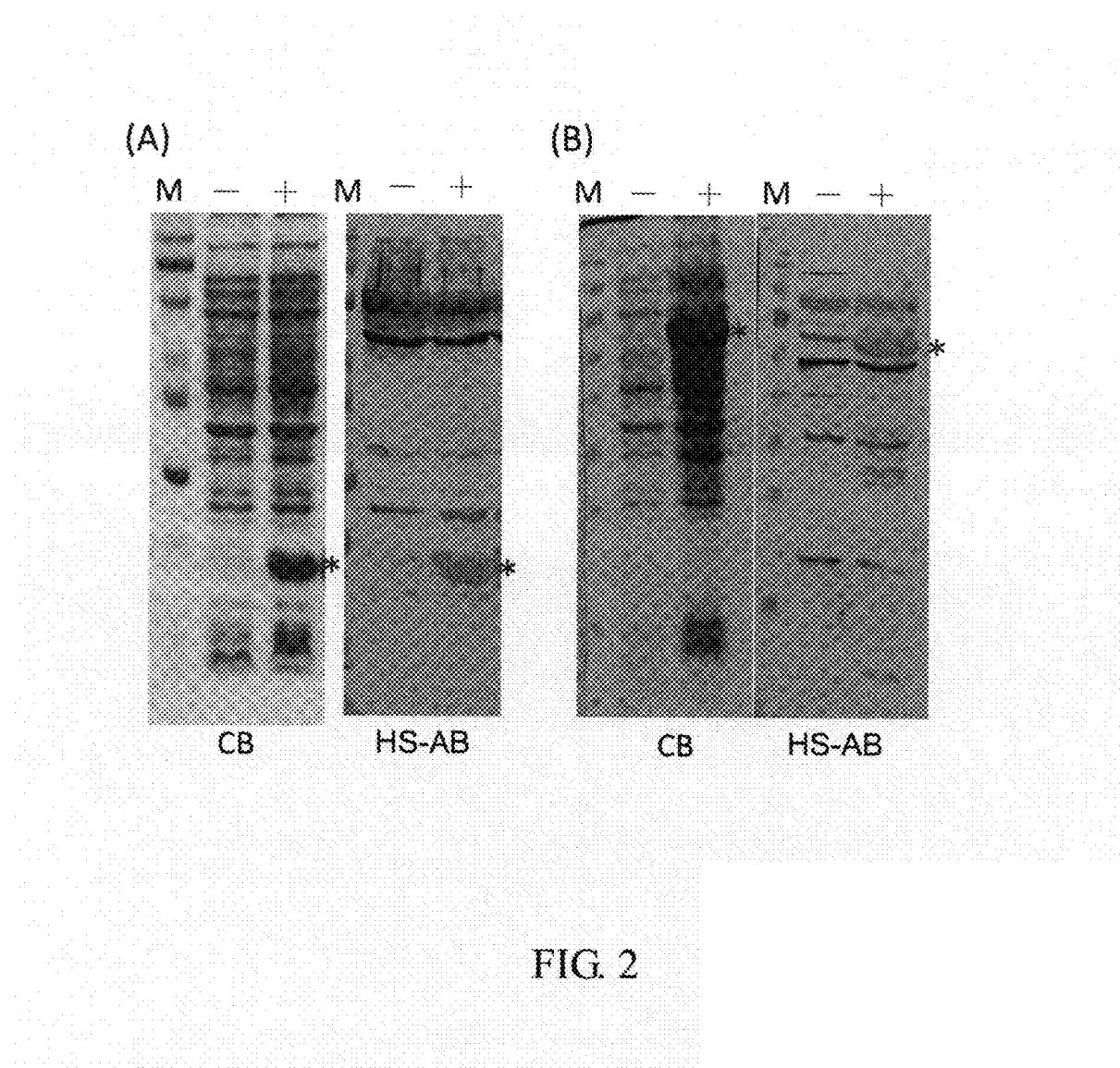
FIG. 2 shows the results of Western blot analysis with human sera and Coomassie blue staining of the recombinant proteins expressed by plasmid (a) pET-NcsP and (b) pET-TonB-R according to Example 1 of the present invention. 'M' represents protein markers, '−' represents no addition of IPTG, '+' represents addition of IPTG to induce protein expression, 'CB' represents coomassie blue, 'HS-AB' represents human sera, and '*' represents target recombinant protein expressed.

After that, the above-mentioned DNA products amplified by PCR were further cloned into pET-21 expression vector (designated as pET-NcsP and pET-TonB-R, respectively), and then which were transformed into *E. coli* BL21 (DE3). IPTG was used to regulate the protein expression, and the recombinant protein expressed was analyzed by Western blot analysis. The recombinant protein expressed was determined by the detection of human serum HS-AB, and the result is shown in FIG. 2. As it shows, the recombinant proteins expressed by the gene of NcsP and TonB-R are both recognized by human serum HS-AB so that NcsP and TonB-R are the target antigens of HS-AB is confirmed. Additionally, the result is also the first evidence to confirm that YP_001707847/NcsP and YP_001845144/TonB-R are truly expressible in *Acinetobacter baumannii* and have antigenicity so as to be recognized by the antiserum of patients.

In order to confirm whether the genes of NcsP and TonB-R existed in various *Acinetobacter baumannii* strains, Western blot analysis of hundreds of clinical isolates collected in Taiwan was performed. The results show that NcsP and TonB-R both are detected in all these strains. Among them, 10 clones of *Acinetobacter baumannii* strains were randomly selected and sequenced so that all these strains were confirmed to have these two genes. The amino acid sequences of NcsP and TonB-R were further compared to homologous polypeptides encoded by 29 other *Acinetobacter baumannii* strains in GenBank, and the high identity between different strains was found. Referring to Table 2, the amino acid sequence identities of NcsP (SEQ ID NO: 1) between various *Acinetobacter baumannii* strains are as high as 99%, and the amino acid sequence identities of TonB-R (SEQ ID NO: 2) between various strains are mostly as high as 99%, while only part of them whose identities are 60% or more. Therefore, NcsP and TonB-R existed universally in various *Acinetobacter baumannii* strains and with high homology between strains.

Example 2

Screening and Identification of Antigens Pase1 and Pase2

The antigens Pase1 and Pase2 were identified by reverse vaccinology in this example. First, the ATCC 17978 genome was searched by the keyword "protease" in a DNA database.

There were found of A1S_2546 and A1S_0699, which were respectively annotated as a "secreted trypsin-like serine protease" (hereinafter referred to as Pase1) and a "putative glycoprotein endopeptidase metalloprotease" (hereinafter referred to as Pase2). By comparison, A1S_2546/Pase1 and A1S_0699/Pase2 both were appeared in various *Acinetobacter baumannii* strains, and the identities of which between various strains are about 96% or more. However, for not knowing their functions, the names of them are different.

In order to confirm whether these two DNA are expressed, the primers for RT-PCR (reverse transcription-PCR) were first designed in accordance with the ATCC 17978 genome, and subsequently the RT-PCR was performed. The resultant products with predicted length were cloned into pGEM-T Easy and sequenced. Owing to the products being obtainable by RT-PCR, Pase1 and Pase2 were confirmed to be actually transcribed.

The amino acid sequences of Pase1 and Pase2 were further compared to homologous polypeptides encoded by 29 other *Acinetobacter baumannii* strains in GenBank, and the high amino acid sequence identity between different strains was also found. Referring to Table 2, the amino acid sequence identities of Pase1 (SEQ ID NO: 3) between various *Acinetobacter baumannii* strains are as high as 95-99%, and the amino acid sequence identities of Pase2 (SEQ ID NO: 4) between various strains are as high as 92-100%. Therefore, Pase1 and Pase2 are existed universally in various *Acinetobacter baumannii* strains and with high homology between strains.

After that, the above-mentioned DNA products amplified by PCR were further cloned into pET-21 expression vector (designated as pET-Pase1 and pET-Pase2, respectively) and then expressed in following example.

Example 3

Survival Test of Mice Immunized with Antigens NcsP, TonB-R, Pase1 and Pase2

To evaluate whether proteins of NcsP, TonB-R, Pase1 and Pase2 are suitable to be included as *Acinetobacter baumannii* vaccine composition, *E. coli* BL21 (DE3) clones, which were respectively transformed with pET-NcsP, pET-TonB-R, pET-Pase1 and pET-Pase2, were incubated and then the IPTG was added to indirectly induce expression of recombinant proteins when the $OD_{600}$ of culture reached 0.8-1.

Figure 3:
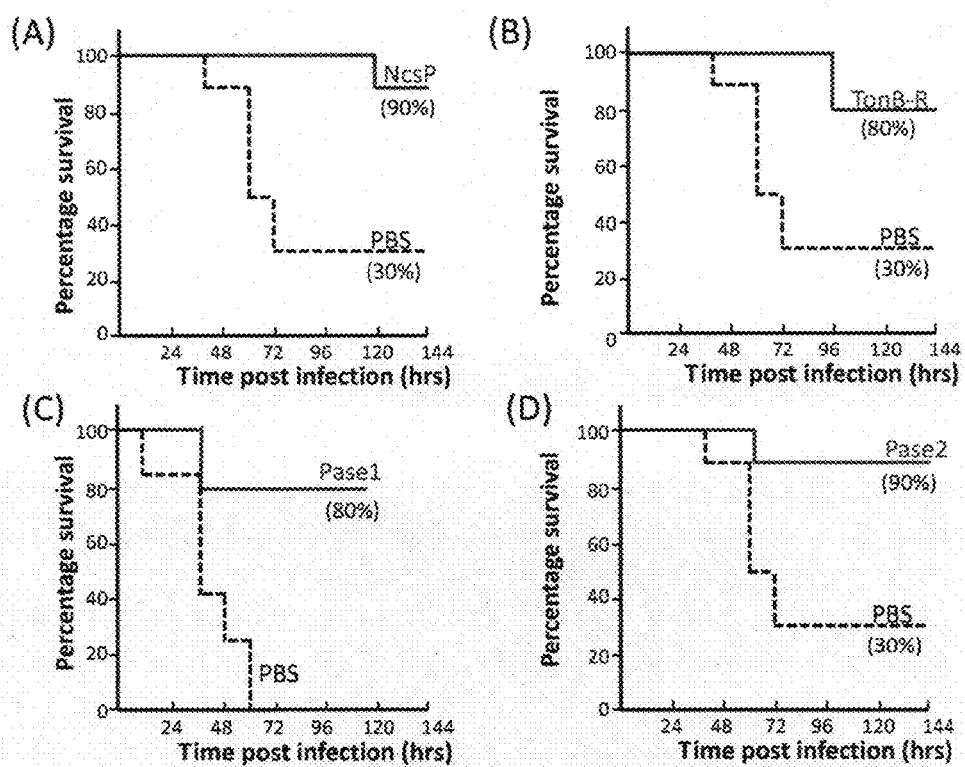
FIG. 3 shows the survival rates of mice immunized with antigen (a) NcsP, (b) TonB-R, (c) Pase1, and (d) Pase2 after challenge test according to Example 3 of the present invention. 'PBS' represents control group.

After that, the resultant recombinant proteins (NcsP, TonB-R, Pase1 and Pase2) were isolated and purified by $Ni^{2+}$-affinity column chromatography. The purity of recombinant proteins was subsequently checked by SDS-PAGE, and then which were applied for mice immunization. In addition, the specificity of antiserum against these recombinant proteins was checked by Western blot analysis and ELISA (enzyme-linked immunosorbent assay). Then, the *Acinetobacter baumannii* ATCC 17978 was used to perform pulmonary challenge test and the survival rates of mice immunized with antigens NcsP, TonB-R, Pase1 and Pase2 were determined. The mice were immunized intraperitoneally with recombinant NcsP, TonB-R, Pase1 or Pase2 in the presence of complete Freund's adjuvant (FA) for the first injection and incomplete FA for the boosting immunization. Mice were challenged with ATCC 17978 after the 3rd immunization, and the results are shown in FIG. 3. As shown in FIG. 3, the 5-day survival rates of the immunized mice are 10-30% (PBS), 90% (NcsP), 80% (TonB-R), 80% (Pase1), and 90% (Pase2), respectively. The 5-day survival rates of mice immunized with the polypeptide antigens according to the present invention are significantly higher than that of control group (PBS). Therefore, the polypeptide antigens according to the present invention can elicit excellent protective immunity in received mice and be qualified to be candidate vaccine compositions. It is noted that although the amino acid sequence identity of the recombinant TonB-R compared to corresponding sequence of ATCC 17978 is only 61%, the effect of protective immunity is still significant.

Example 4

Safety Test of Antigens NcsP, TonB-R, Pase1 and Pase2

Figure 4:
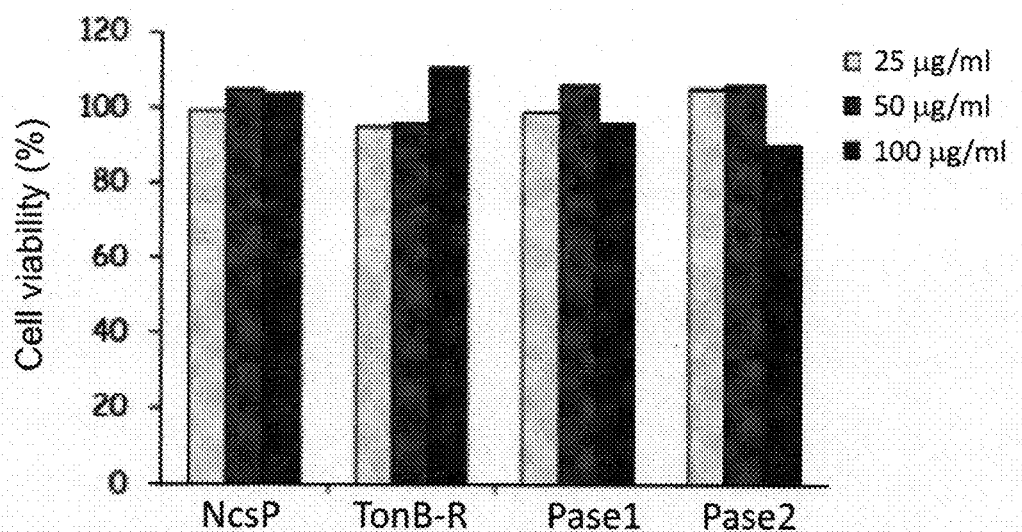
FIG. 4 shows the results of MTT assay regarding polypeptide antigens according to Example 4 of the present invention.
Figure 5:
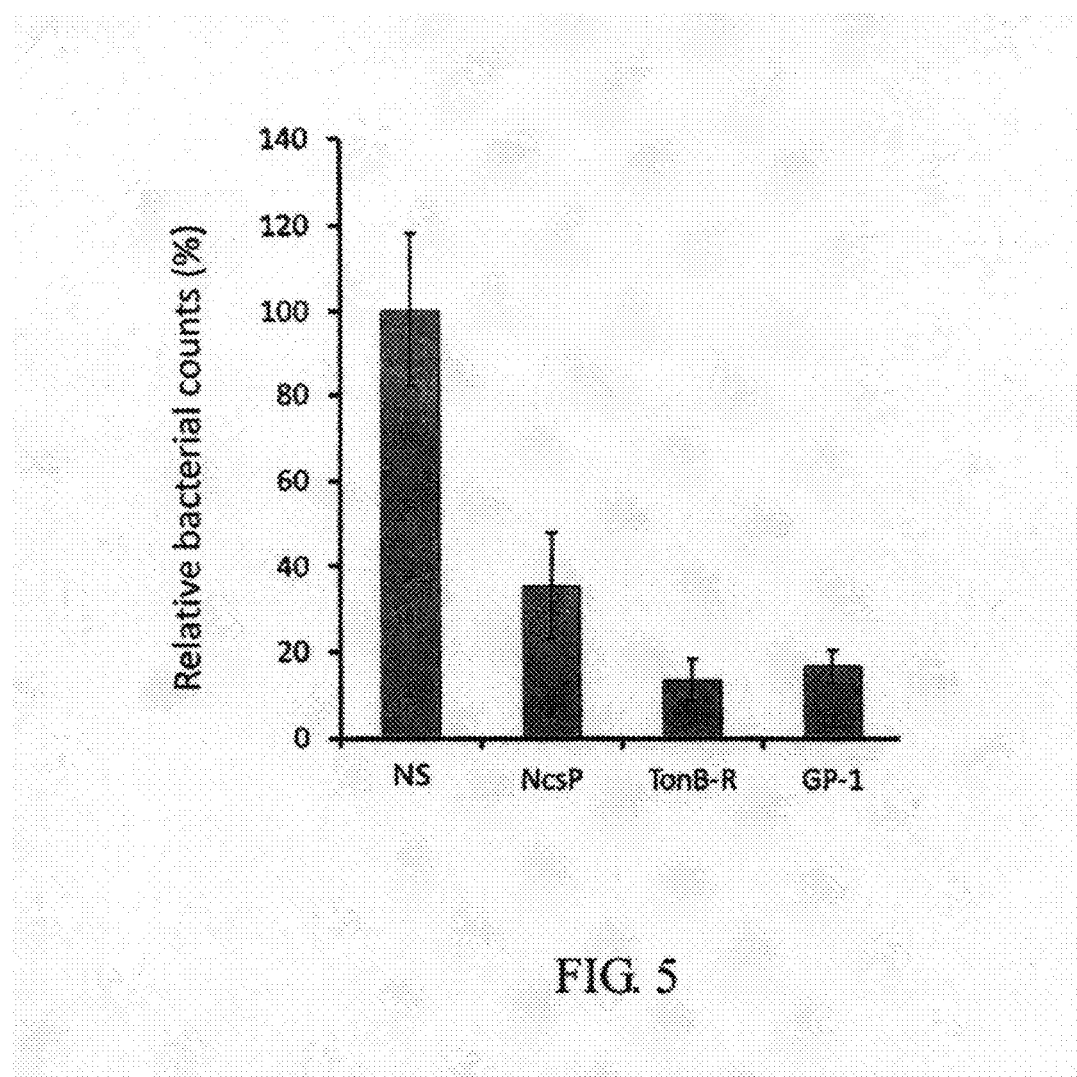
FIG. 5 shows the results of bactericidal test of anti-GP1 antiserum according to Example 6 of the present invention. 'NS' represents normal serum.
Figure 6:
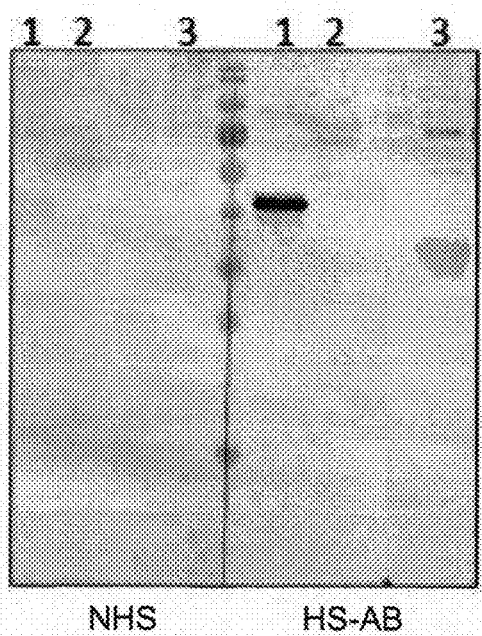
FIG. 6 shows the results of Western blot analysis of the recombinant protein GP1 with human sera according to Example 6 of the present invention. Lanes: 1—outer membrane protein A of *Acinetobacter baumannii;* 2—TonB-R; and 3—GP1. 'NHS' represents normal human sera (left panel) (control). 'HS-AB' represents sera of a patient infected with *Acinetobacter baumannii* (right panel).

To confirm whether polypeptide antigens according to present invention are cytotoxic or not, human lung adenocarcinoma epithelial cells A549 were provided and treated with the purified recombinant proteins (NcsP, TonB-R, Pase1 and Pase2), and then analyzed by MTT assay. The MTT assay may refer to as described in the Book of Sambrook et al. (Sambrook et al., Molecular Cloning). The results are shown in FIG. 4. The results indicate that all these four antigens are not cytotoxic to A549 cells. They are good and safety polypeptide antigens, and are suitably included as vaccine composition for prevention of *Acinetobacter baumannii* infection.

In addition, although Pase1 and Pase2 were annotated as "tyrpsin-like proteases", no protease activity was detected with up to 0.5 mg/mL of the purified recombinant proteins using QuantiCleave™ protease assay kit. Combining this feature with the result of MTT assay, Pase1 and Pase2 were further confirmed to be non-cytotoxic.

Based on above results, it can be determined that NcsP, TonB-R, Pase1 and Pase2 are all "expressible" in various *Acinetobacter baumannii* strains, which is not known and has not disclosed or taught. Since the amino acid sequence identities between *Acinetobacter baumannii* strains were high, the protective immunity should all be elicited against infections of different *Acinetobacter baumannii* strains. In addition, with high safety and no cytotoxicity, NcsP, TonB-R, Pase1 and Pase2 all are sufficient to be the antigen candidates of broad-spectrum vaccines against *Acinetobacter baumannii*.

Example 5

Screening and Identification of Antigen GP1

The antigen GP1 was identified by reverse vaccinology in this example. First, the amino acid sequence of A1S 0556 (hereinafter referred to as GP1) was analyzed by DOLOP (Database of bacterial lipoproteins). The result shows that there is a leader sequence of lipidation signal, thereby GP1 was predicted to be a lipoprotein. Besides, Iwashkiw et al. have found that GP1 in ATCC 17978 is modified by glycosylaion (Iwashkiw J A, Seper2 A, Weber B S, Scott N E, Vinogradov E, Stratilo C, Reiz B et al., 2012. Identification of a general O-linked protein glycosylation system in *Acinetobacter baumannii* and its role in virulence and biofilm formation. PLoS Pathogens, 2012). In this example, the DNA fragment encoding amino sequence of GP1 from amino acid residue at positions 39 to 313 was amplified by PCR, and then cloned into pET21 expression vector. By subsequent transformation to *E. coli* BL21 (DE3), the GP1 gene was indirectly induced to express recombinant protein by adding IPTG. The expressed recombinant protein was isolated and purified by $Ni^{2+}$-affinity column chromatography. The purified recombinant protein was then used to immunize mice. Following immunization, Western blot analysis was performed by using the antiserum collected from immunized mice to react with total proteins of Taiwan *Acinetobacter baumannii* clinical isolates. The results shown that the GP1 can be detected in all tested *Acinetobacter baumannii* strains. Furthermore, the amino acid sequence of GP1 was compared to homologous polypeptides encoded by 29 other *Acinetobacter baumannii* strains in GenBank. Consequently, the amino acid sequence identity is as high as 95-99% between different strains (see Table 2). That is to say, GP1 is also proved to be one conserved antigen of *Acinetobacter baumannii.*

Example 6

Bactericidal Test of Antiserum Collected from Mice Immunized with GP1 Antigen To evaluate whether GP1 protein can be comprised as *Acinetobacter baumannii* vaccine composition, not only performing the survival test in vivo by challenging mice with ATCC 17978 as previously state, the in vitro bactericidal test of ATCC 17978 by antibodies induced by the polypeptide antigen is also a common method for determining the effectiveness of a vaccine.

Therefore, in this example, the recombinant GP1 purified by $Ni^{2+}$-affinity column chromatography was used to immunize mice, and then the antiserum (anti-GP1) recovered was used to perform bactericidal test. Approximately 100 CFU of *Acinetobacter baumannii* was incubated in 50% anti-GP1/PBS medium at 37° C. for 4 hours. The number of viable *Acinetobacter baumannii* was determined, and the results are shown in FIG. 5. As seen from the figure, the viable number of *Acinetobacter baumannii* in the group treated with anti-GP1 is significantly lower than that of control group (the serum used in the control is from pre-immunized mice). The effect of anti-GP1 (about 18%) is even better than that of anti-NcsP (about 35%), and thus it is determined that GP1 has excellent bactericidal effect. Accordingly, GP1 is proved to be capable of inducing a protective immune response, and can be an effective antigen comprised in a vaccine. In addition, by Western blot analysis, in which the serum of patient infected with *Acinetobacter baumannii* was directed to recombinant GP1, and a specific recognizing signal was detected and shown in FIG. 6. The results demonstrate that the GP1 indeed is capable of eliciting human immune response, and can serve as a vaccine composition.

Example 7

Preparation of Monoclonal Antibodies

Preparation of monoclonal antibodies can be performed by known method in the art. The above-mentioned recombinant/polypeptide antigens or fragments thereof were purified by $Ni^{2+}$-affinity column chromatography. The BALB/c mice were then immunized with the protein/polypeptide antigens in the presence of complete Freund's adjuvant for the first injection and incomplete FA for the boosting immunization. The interval is three times per month, and the dose is 10-15 μg each time. After 4 days of the last boosting, the spleen of the mice was taken out, and the spleen cells thereof were fusion with myeloma Sp2/0-Ag14. Subsequent screening of live hybridoma cells was performed with ELISA and Western blot analysis to obtain cell clones with specificities.

The monoclonal antibody raised against each recombinant protein/polypeptide antigen of the present invention, derivate or fragment thereof can be included in a diagnostic kit to detect the presence of *Acinetobacter baumannii* in a sample. The detection method can be performed by common skills in the art. The monoclonal antibody can be mixed with a specimen to analyze the binding between antibody and antigen to determine the presence of *Acinetobacter baumannii* in the specimen by absorbance or fluorescence using reagents and instruments.

The above-mentioned monoclonal antibodies comprised in the diagnostic kit can be one monoclonal antibody directed against one polypeptide antigen, two or more monoclonal antibodies directed against one polypeptide antigen, or multiple monoclonal antibodies directed against two or more polypeptide antigens. By multiple detection, the detecting accuracy can be increased Moreover, not only the monoclonal antibody against the polypeptide antigen, the polyclonal antibody or fragment thereof against the polypeptide antigen all can be used to treat the patient infected with *Acinetobacter baumannii*. For preparing a pharmaceutical composition, effective amount of previous described antibodies can be provided and/or formulated with a pharmaceutically acceptable carrier.

The antibody contained in pharmaceutical composition is preferably monoclonal antibody. As described above, the antibody used can be one monoclonal antibody directed against one polypeptide antigen, or two or more monoclonal antibodies directed against two or more polypeptide antigens.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An isolated polypeptide antigen of *Acinetobacter baumannii*, consisting of the amino acid sequence of:
    positions 39 to 313 of SEQ ID NO: 5
    for use in the treatment of *Acinetobacter baumannii* related infections by vaccinating the polypeptide antigen in a subject for inducing an effective immune protection.

2. A method for inducing an immune response against *Acinetobacter baumannii* in a subject comprising: administering to the subject a composition comprising the polypeptide antigen of claim 1, wherein the subject administered with the polypeptide antigen can produce an effective immune protection against *Acinetobacter baumannii* related infections.

3. A vaccine composition comprising at least a polypeptide antigen of claim 1.

* * * * *

SEQUENCE LISTING

```
<160> NUMBER OF SEQ ID NOS: 10

<210> SEQ ID NO 1
<211> LENGTH: 157
<212> TYPE: PRT
<213> ORGANISM: Acinetobacter baumannii

<400> SEQUENCE: 1

Met Gly Leu Phe Asp Phe Val Lys Gly Ile Gly Lys Lys Asn Thr Ala
1               5                   10                  15

Pro Ala Glu Pro Gln Ala Ala Pro Ala Thr Pro Ala Glu Pro Ser Ala
            20                  25                  30

Gln Glu Ile Ala Asn Lys Leu Leu Gly Leu Ile Lys Ser Leu Gly Leu
        35                  40                  45
```

```
Gly Val Glu Gly Leu Ser Val Thr Tyr Asn Gly Ser Thr Asp Thr Ala
     50                  55                  60

Ile Ile Lys Gly Gln Val Gln Ser Gln Ala Asp Lys Glu Lys Ile Ile
 65                  70                  75                  80

Leu Ile Val Gly Asn Val Asp His Val Ala Gln Val Asp Asp Gln Met
                 85                  90                  95

Thr Val Ala Thr Pro Glu Pro Glu Ser Lys Phe Tyr Thr Val Lys Ser
            100                 105                 110

Gly Asp Asn Leu Ser Lys Ile Ala Lys Glu Phe Tyr Gly Asp Ala Asn
                115                 120                 125

Arg Tyr Gln Lys Ile Phe Glu Ala Asn Lys Pro Met Leu Lys Asp Pro
130                 135                 140

Asp Glu Ile Phe Pro Gly Gln Val Leu Arg Ile Pro Gln
145                 150                 155

<210> SEQ ID NO 2
<211> LENGTH: 743
<212> TYPE: PRT
<213> ORGANISM: Acinetobacter baumannii

<400> SEQUENCE: 2

Met Ser Leu Ile Arg Thr Arg Lys Lys Ile Val Ser Ser Ala Ile Ala
 1                5                  10                  15

Ser Ser Leu Ser Met Ile Ala Thr Thr Ala Met Ala Gln Glu Ala Val
                 20                  25                  30

Ser Gln Leu Pro Thr Ile His Thr Lys Ala Thr Gln Glu Glu Ser Leu
             35                  40                  45

Lys Val Asp Gln Ser Ala Asn Ser Lys Phe Val Ala Pro Leu Leu Asp
 50                  55                  60

Thr Pro Lys Ser Val Ser Val Ile Ser Lys Gln Leu Ile Glu Asp Thr
 65                  70                  75                  80

Lys Val Thr Thr Leu Ala Asp Ala Leu Arg Thr Val Pro Gly Ile Thr
                 85                  90                  95

Leu Gly Ala Gly Glu Gly Gly Asn Pro Asn Gly Asp Arg Pro Phe Ile
            100                 105                 110

Arg Gly Tyr Ser Ser Glu Ser Ser Met Tyr Ile Asp Gly Ile Arg Asn
                115                 120                 125

Ser Thr Ser Gln Asn Arg Glu Met Phe Ala Val Glu Gln Val Glu Val
            130                 135                 140

Thr Lys Gly Ser Ala Ser Ala Met Gly Gly Ala Gly Ser Val Gly Gly
145                 150                 155                 160

Ser Ile Asn Met Ile Ser Glu Val Ala Lys Lys Gly Asp Phe Leu Glu
                165                 170                 175

Gly Ser Val Ala Ala Gly Thr Asp Asn Tyr Gln Arg Ile Thr Leu Asp
            180                 185                 190

Gly Asn Lys Asp Phe Gly Asn Gly Ile Ala Ala Arg Val Ala Val Leu
                195                 200                 205

Gly His Gln Asn Glu Lys Ala Val Gln Ser Asn Gly Ala Glu Tyr Lys
            210                 215                 220

Arg Val Gly Ile Ala Pro Ser Ile Thr Phe Gly Leu Asp Thr Pro Thr
225                 230                 235                 240

Arg Ala Thr Leu Ser Tyr Tyr Leu Gln Thr Asp Asp Lys Pro Asp
                245                 250                 255

Ser Gly Ile Pro Tyr Trp Asp Ser Ser Leu Gly Lys Ala Gln Gly Lys
            260                 265                 270
```

```
Pro Ala Glu Val Lys Gln Gly Thr Tyr Tyr Gly Trp Lys Asp Arg Asp
            275                 280                 285

Phe Gln Lys Gln Glu Asn His Ile Gly Thr Ile Lys Leu Glu His Asp
        290                 295                 300

Leu Thr Asp Asn Ile Thr Ile Thr Asn Thr Ala Met Tyr Ala Lys Ser
305                 310                 315                 320

Lys Asn Asp Tyr Val Trp Thr Asn Pro Asp Asp Ser Lys Gly Asn Val
                325                 330                 335

Gly Lys Gly Leu Val Trp His Arg Leu Ser Ser Ala Ile Thr Asp Ser
            340                 345                 350

Glu Thr Phe Thr Asp Gln Leu Ala Leu Thr Gly Lys Phe Asp Thr Gly
        355                 360                 365

Phe Leu Lys His Arg Phe Asn Val Gly Ala Glu Tyr Ser Lys Gln Lys
        370                 375                 380

Thr Asp Lys Gly Gly Tyr Asn Ile Ile Asp Ala Lys Gly Asn Val Ser
385                 390                 395                 400

Ser Thr Gly Phe Tyr Ser Asp Cys Ser Asp Leu Ser Thr Asn Trp Cys
                405                 410                 415

Thr Ser Leu Asn Gly Pro Thr Gln Lys Pro Phe Val Asp Arg Leu Gln
            420                 425                 430

Ala Arg Pro Asp Phe Asp Ala Thr Val Glu Ser Thr Val Tyr Leu
        435                 440                 445

Leu Asp Asn Ile Glu Ile Thr Pro Lys Trp Leu Leu Asp Leu Gly Leu
        450                 455                 460

Arg Trp Asp Lys Phe Glu Ala Glu Gln Asn Phe Leu Ala Thr Ser Ser
465                 470                 475                 480

Ala Ala Ala Tyr Thr Ala Lys Asn Asp Ser Asp Phe Val Thr Tyr Gln
                485                 490                 495

Ala Gly Ile Thr Phe Lys Pro Thr Glu Asn Gly Ser Ile Tyr Thr Ser
            500                 505                 510

Tyr Ala Thr Ser Ala Ser Pro Val Gly Leu Asn Ala Gly Trp Gly Asp
        515                 520                 525

Asn Ser Glu Thr Ile Asn Ala Asn Asn Gln Met Ile Asp Pro Glu Glu
        530                 535                 540

Ala Gln Thr Phe Glu Ile Gly Thr Lys Trp Asp Phe Leu Asp Asn His
545                 550                 555                 560

Leu Asn Leu Thr Ala Ala Ile Phe Arg Thr Glu Lys Gln Asn Thr Arg
                565                 570                 575

Val Gln Ile Asp Pro Thr Thr Tyr Ala Asn Val Gly Glu Ser Lys Val
            580                 585                 590

Asp Gly Phe Glu Leu Gly Leu Asn Gly Glu Ile Thr Asp Lys Trp Asn
        595                 600                 605

Ile Ser Ala Gly Tyr Thr Tyr Leu Asp Ser Glu Leu Thr Lys Asn Gly
        610                 615                 620

Lys Ser Cys Arg Ser Gly Lys Cys Thr Asp Gln Ser Ile Tyr Asn Gly
625                 630                 635                 640

Asn Gln Met Pro Asn Val Pro Lys Gln Ala Ala Thr Leu Trp Thr Thr
                645                 650                 655

Tyr Arg Val Leu Pro Gln Leu Thr Val Gly Ala Gly Ala Val Tyr Ser
            660                 665                 670

Asp Lys Val Tyr Gly Asp Val Ala Asn Thr Lys Trp Val Pro Ser Tyr
        675                 680                 685
```

```
Val Arg Tyr Asp Ala Met Ala Arg Tyr Asn Val Asn Lys Asn Val Asp
    690                 695                 700

Leu Gln Leu Asn Ile Asn Asn Leu Ser Asp Lys Arg Tyr Phe Thr Lys
705                 710                 715                 720

Ala Tyr Ala Ser His Tyr Ala Thr Glu Ala Glu Gly Arg Ser Ala Val
                725                 730                 735

Leu Ala Val Asn Phe Lys Tyr
            740

<210> SEQ ID NO 3
<211> LENGTH: 132
<212> TYPE: PRT
<213> ORGANISM: Acinetobacter baumannii

<400> SEQUENCE: 3

Met Leu Asn Ala Ile Asn Gln Ile Arg Gln Asp Ser Arg Gln Cys Gly
1               5                   10                  15

Gln Gln Tyr Phe Ser Ala Ala Lys Pro Leu Ser Trp Asn Asn Asn Leu
            20                  25                  30

Tyr Gln Gly Ala Asn Ala His Ser Lys Asp Met Ala Asn Asn Asn Phe
        35                  40                  45

Leu Gly His Val Gly Ser Thr Gly Leu Asp Leu Arg Ala Arg Leu Lys
    50                  55                  60

Lys Tyr His Met Leu Ser Lys Ala Asn Gly Glu Asn Val Ala Ser Gly
65                  70                  75                  80

Gln Lys Thr Leu Asn Glu Val Met Ala Lys Trp Ile Ala Ser Pro Leu
                85                  90                  95

His Cys Ser Asn Ile Met Asn Pro Arg Tyr Thr Glu Tyr Ala Ile Ala
            100                 105                 110

Cys Ala Ser Asp Gln Ser Ala Lys Gln Arg Ser Tyr Trp Thr Gln Gln
        115                 120                 125

Phe Ala Gly Phe
    130

<210> SEQ ID NO 4
<211> LENGTH: 180
<212> TYPE: PRT
<213> ORGANISM: Acinetobacter baumannii

<400> SEQUENCE: 4

Met Ile Glu Gln Gly Leu Gln Gln Thr Gly Leu Asp Val Ala Gly Leu
1               5                   10                  15

Asp Ala Ile Ala Phe Ser Arg Gly Pro Gly Ser Phe Ser Gly Val Arg
            20                  25                  30

Ile Asn Ala Ala Val Ala Gln Ala Leu Ala Trp Ser Gln Asp Leu Pro
        35                  40                  45

Val Ile Pro Val Ser Thr Leu Gln Ala Leu Ala Gln Ala Ala Tyr Arg
    50                  55                  60

Leu Lys Gly Leu Glu Gln Val Thr Ala Val Leu Asp Ala Arg Met Asn
65                  70                  75                  80

Glu Val Tyr Ile Ala Ser Phe Val Leu Asp Glu Gln Gly Ile Met Gln
                85                  90                  95

Cys Ile Asp Glu Glu Lys Leu Met Asn Tyr Glu Gln Ala Ala Ala Tyr
            100                 105                 110

Ala Lys His Cys Leu Ile Gly Ser Gly Ala Lys Leu Leu Gln Thr Asp
        115                 120                 125
```

Ala Glu Tyr Gln Thr Ile Thr Ala Thr Ala Gln Asp Ile Ala Ser Ile
130                 135                 140

Ala Arg Val Tyr Ala Ala Gln Lys Gln Trp Val Asp Ala Glu His Ala
145                 150                 155                 160

Leu Pro Val Tyr Leu Arg Asp Asp Ala Trp Lys Lys Ile Ala Asp Gln
                165                 170                 175

Gly Lys Ala Asn
            180

<210> SEQ ID NO 5
<211> LENGTH: 313
<212> TYPE: PRT
<213> ORGANISM: Acinetobacter baumannii

<400> SEQUENCE: 5

Met Leu Thr Ser Lys Ala Ser Leu His Leu Thr Leu Leu Ala Ser Ala
1               5                   10                  15

Ile Phe Leu Val Ala Cys Gln Pro Lys Ser Asp Pro Lys Glu Ser Glu
                20                  25                  30

Asp Gln Gln Lys Pro Ala Val Val Glu Gln Lys Pro Val Glu Leu Thr
            35                  40                  45

Leu Lys Gly Glu Thr Val Pro Ser Lys Val Thr Leu Pro Asp Cys Asp
50                  55                  60

Gly Lys Thr Cys Pro Glu Phe Thr Val Glu Arg Leu Gln Ser Asn Phe
65                  70                  75                  80

Pro Phe Ile Asp Lys Ile Ile Asp Gln Gln Val Leu Lys Ala Leu Gly
                85                  90                  95

Gln Ile Leu Glu Ile Ala Glu Pro Asp Ala Lys Ala Ala Gln Ala Asp
            100                 105                 110

Lys Lys Thr Glu Ala Ser Ala Ala Thr Thr Glu Gln Gln Asp Ser
            115                 120                 125

Phe Asp Ala Gln Val Gln Arg Tyr Ala Asn Ser Phe Ile Asp Leu Asp
130                 135                 140

Asn Glu Leu Lys Ala Leu Ser Ser Asn His Gln Ile Asn Leu Leu Val
145                 150                 155                 160

Lys Pro Lys Ile Ile Gln Ser Gln Gly Lys Val Val Thr Val Val Val
                165                 170                 175

Asn Ser Ser Ser Tyr Leu Gly Gly Ala His Gly Ser Ala Ala Gln Gln
            180                 185                 190

Tyr Tyr Asn Phe Asp Leu Lys Lys Glu Lys Gln Val Lys Leu Glu Asp
            195                 200                 205

Leu Leu Arg Pro Glu Lys Lys Ala Ala Leu Glu Lys Leu Ala His Glu
210                 215                 220

Ala Phe Lys Ala Trp Val Thr Asp Ser Lys Leu Ala Asn Ser Val Ser
225                 230                 235                 240

Glu Tyr Glu Gln Ala Trp Pro Phe Lys Leu Thr Glu Asn Phe Leu Leu
                245                 250                 255

Gly Asp Gln Gly Leu Ile Leu Gln Tyr Gly Glu Tyr Glu Ile Gly Pro
            260                 265                 270

Tyr Val Val Gly Leu Pro Arg Leu Val Ile Pro Tyr Asp Gln Leu Gln
            275                 280                 285

Glu Val Leu Lys Glu Glu Tyr Leu Pro Gln Lys Ala Lys Pro Ala
290                 295                 300

Ser Thr Pro Ala Val Lys Ser Ala Ser
305                 310

```
<210> SEQ ID NO 6
<211> LENGTH: 471
<212> TYPE: DNA
<213> ORGANISM: Acinetobacter baumannii

<400> SEQUENCE: 6
atgggtcttt tgattttgt aaaaggtatt ggtaagaaaa ataccgcacc agcagaacca      60
caagcagctc cagcaacacc agcagaacct tctgcacaag aaattgcgaa taaattattg     120
ggattgatta aaagcttagg ccttggggtg aaggcttat ctgtaacata taatggctca     180
actgacactg ctattattaa aggacaagtc caaagccaag cagataaaga aaaaatcatt     240
cttattgtgg gtaatgtaga tcatgtggca caagtagatg accagatgac tgttgcaact     300
cctgagccag aaagcaaatt ttatacagtg aaatctggtg ataatctttc aaaaattgct     360
aaagagtttt atggtgatgc caatcgatat caaaaaatct tgaagcgaa taaaccaatg      420 ctgaaagatc cagatgagat ttttccagga caagttttac gtattcctca g             471

<210> SEQ ID NO 7
<211> LENGTH: 2229
<212> TYPE: DNA
<213> ORGANISM: Acinetobacter baumannii

<400> SEQUENCE: 7
atgtcattga ttagaacacg taaaaaaatt gtttcctctg caatcgcctc atcgctctcg      60
atgatagcaa caactgcgat ggcgcaagaa gcagtttcgc aattaccaac tatccatact     120
aaagcgactc aagaagaatc tttaaaggtt gatcaatcag caaactctaa atttgttgct     180
ccccttctag atactcctaa atcagtatca gttatctcaa acaacttat agaagatacc     240 aaagtaacaa ctttagcaga tgcattgcgt actgttcctg gcattacttt aggtgcaggt     300
gaaggcggta atccgaatgg tgatcgacct tcatccgtg gttatagttc agaaagctct     360
atgtatattg atggtatccg caactctacc tcacaaaacc gtgaaatgtt tgcggtcgag     420
caagtagagg taaccaaagg ttctgcatca gcaatgggtg gtgcaggttc agttggtggc     480
agcatcaata tgatttccga ggtagctaaa aagggtgatt ttctagaagg ctcagtagcc     540
gctggtactg ataactacca acgtatcact ttagatggta taaagacttt ggaaatggc     600 attgcagcac gtgtagctgt tttgggacat caaaatgaaa aggctgtcca agtaatggg     660 gctgaatata aacgtgttgg tattgcacca agtattactt ttggcttaga tacaccgaca     720
cgtgcaactt tgagctacta ttatttacaa actgatgata aacctgattc aggtattcct     780
tattgggatt catctcttgg aaaagctcaa ggtaaaccgg ctgaagtcaa acaaggtaca     840
tattacggct ggaaagatcg agatttcaa agcaagaaa atcacatcgg tacaattaaa     900
ttagaacacg accttaccga caatataact attactaata cggccatgta tgccaaatca     960
aaaaatgatt atgtctggac aaacccagat gactcaaaag gtaatgttgg caaaggtctt    1020
gtttggcatc gtttgagctc agctattaca gatagtgaga catttaccga tcaattagca    1080
cttacaggta aatttgatac tggcttctta aagcacagat ttaatgtagg agcagagtac    1140
agcaaacaaa aaactgataa aggcggctat aacattattg atgccaaagg taatgtttct    1200
agtactggct tctatagcga ttgttcagac ttatcaacaa attggtgtac ttcgctcaat    1260
ggtccaactc aaaagccatt tgttgaccgt ttacaagcac gcccagactt tgatgcaact    1320
gtagaaagta cttctgtcta cttactcgac aatattgaga tcacaccaaa atggttatta    1380
gatcttggcc tacgttggga taagtttgaa gctgaacaaa acttcttagc cacttctagt    1440
```

| | |
|---|---|
| gcagcggcct atacagcaaa aaatgattca gatttcgtga cctatcaagc gggcattaca | 1500 |
| tttaaaccaa cagagaatgg ctcaatttat acaagctatg caacctcagc tagtccagtc | 1560 |
| ggcttaaatg caggttgggg ggataatagc gaaacaatta atgccaataa tcaaatgatt | 1620 |
| gatcccgaag aggcacaaac atttgaaatc ggtacgaaat gggatttcct agataaccac | 1680 |
| ctaaatttaa cagctgctat tttccgtact gaaaaacaaa atacacgtgt acaaatcgac | 1740 |
| ccaactactt atgcaaatgt aggtgaaagt aaagttgatg gttttgaatt aggcttaaat | 1800 |
| ggtgaaatta ctgataaatg gaacatttca gctggctata cttatttaga cagtgaacta | 1860 |
| accaaaaatg gtaaatcttg ccgtagcgga aaatgtactg accaatccat ttataatggc | 1920 |
| aaccaaatgc caaacgtacc taagcaagct gctacgttat ggactaccta tagagtactt | 1980 |
| ccacaattga cggtaggcgc tggcgctgtt tactctgaca agtatatgg tgatgtagca | 2040 |
| aatactaaat gggttccatc ttacgtacgt tacgatgcga tggcacgtta caacgtaaat | 2100 |
| aaaaatgttg atcttcaatt aaatatcaac aacctatctg ataagcgcta tttcactaaa | 2160 |
| gcttacgctt ctcactatgc aacagaagca gaaggccgta gtgcagttct agcagttaac | 2220 |
| tttaaatac | 2229 |

<210> SEQ ID NO 8
<211> LENGTH: 396
<212> TYPE: DNA
<213> ORGANISM: Acinetobacter baumannii

<400> SEQUENCE: 8

| | |
|---|---|
| gtgcttaatg caattaatca aattcgacaa gattctcgtc aatgtggtca gcagtatttt | 60 |
| tctgcagcta aacctttaag ctggaataat aatttatatc aaggtgcaaa tgctcactct | 120 |
| aaagatatgg caaataacaa ctttctcggg catgttggct caacaggttt agatttaaga | 180 |
| gcgagattaa aaaaatatca tatgctgagt aaagccaatg gtgagaatgt cgcgagtgga | 240 |
| caaaaaactt taaatgaggt catggctaaa tggatcgcca gtcctctgca ttgcagtaat | 300 |
| atcatgaacc ctagatatac cgaatatgcc attgcatgtg cttctgacca gtctgctaaa | 360 |
| caaagaagct attggacaca acaatttgca ggtttt | 396 |

<210> SEQ ID NO 9
<211> LENGTH: 540
<212> TYPE: DNA
<213> ORGANISM: Acinetobacter baumannii

<400> SEQUENCE: 9

| | |
|---|---|
| atgattgagc aaggattaca acaaactgga cttgacgtag ctggtttaga tgcaattgcc | 60 |
| tttagtcgag ggcccggttc ttttagtggt gttcgaatta atgcagcagt tgctcaagct | 120 |
| ttagcttggt cacaagattt accagtaatt ccagtttcta ccttacaggc tctcgcacaa | 180 |
| gcggcttacc gacttaaagg tttagaacag gtgactgcgg tactcgatgc acgtatgaat | 240 |
| gaagtttaca ttgcaagttt tgttctagat gagcaaggca tcatgcagtg tatagatgaa | 300 |
| gaaaaattaa tgaactacga gcaagcggct gcctatgcaa agcattgcct aatcggttcg | 360 |
| ggcgctaagc tccttcaaac tgatgcagaa tatcaaacaa tcactgccac tgcacaagac | 420 |
| attgcttcga ttgcacgtgt gtatgcagcg caaaagcagt gggttgatgc tgaacatgct | 480 |
| ttaccagttt acttgcgtga tgatgcatgg aaaaaaattg cggatcaggg caaagcaaat | 540 |

```
<210> SEQ ID NO 10
<211> LENGTH: 939
<212> TYPE: DNA
<213> ORGANISM: Acinetobacter baumannii

<400> SEQUENCE: 10
atgttaactt ctaaggcttc gctacattta acgctacttg cttctgcgat attttttggtg      60 gcatgtcagc ctaaaagtga tcctaaagag tcggaagatc agcaaaaacc ggctgtggtt     120
gaacaaaagc ctgtagaact gactttgaaa ggagaaacag ttccaagtaa agtgacttta     180
ccggattgtg atggtaaaac ttgtcctgaa tttacggtag aacgcctaca aagtaatttc     240 cctttattg ataagattat tgatcaaca gttttaaaag cactcggtca gattcttgaa      300
attgcagaac cagatgcaaa agcagcacaa gctgataaga agacagaagc ttcagcagct     360
gccactacag agcaacaaga tagtttcgat gctcaggttc agcgctatgc aaattcattt     420
attgatttgg acaatgagtt aaaggctcta agtagtaatc accagattaa tctgttggtg     480
aaacctaaaa tcatacagtc tcaaggtaaa gtcgtaactg ttgttgtaaa tagtagtagc     540
tatttaggcg gggcacatgg ctcggcagcg cagcaatatt ataattttga cttaaagaaa     600
gaaaagcagg tcaaacttga agacttgtta cgtccagaga aaaaagcggc tttagaaaaa     660
ttagcacatg aagcgtttaa agcttgggtg acagactcaa aacttgcaaa tagtgtgagt     720
gaatatgagc aagcttggcc gtttaaactc acagaaaatt ttctgttagg tgaccaaggc     780
ttgattcttc aatatggcga atatgaaatt ggaccttatg tggtcgggct acctcgttta     840
gtcattccat atgaccaatt acaagaagta ttgaaagaag aatatttgcc gcagcctaaa     900
gctaaaccag cttcgacacc tgccgtaaaa agtgccagc                            939
```